United States Patent

Rütter et al.

[11] Patent Number: 5,942,645
[45] Date of Patent: Aug. 24, 1999

[54] HYDROGENATION OF AROMATIC COMPOUNDS IN WHICH AT LEAST ONE HYDROXYL GROUP IS BONDED TO AN AROMATIC RING

[75] Inventors: Heinz Rütter, Hochdorf-Assenheim; Thomas Rühl, Frankenthal; Boris Breitscheidel, Fulda; Jochem Henkelmann, Mannheim; Thomas Wettling, Limburgerhof, all of Germany

[73] Assignee: BASF Aktiengesellschaft, Ludwigshafen, Germany

[21] Appl. No.: 08/794,574

[22] Filed: Feb. 3, 1997

[30] Foreign Application Priority Data

Feb. 9, 1996 [DE] Germany ............... 196 04 791

[51] Int. Cl.$^6$ .................................................. C07L 35/08
[52] U.S. Cl. .................. 568/832; 568/716; 568/822; 568/830; 568/835; 568/376; 502/330; 502/335; 502/337
[58] Field of Search ...................... 568/716, 822, 568/832, 376, 830, 835; 502/330, 335, 337

[56] References Cited

U.S. PATENT DOCUMENTS 2,927,127   3/1960   Somerville et al. ............. 260/488
3,966,833   6/1976   Cosyns et al. ................... 260/672
4,343,955   8/1982   Oshima et al. ................... 568/834
4,424,162   1/1984   Rosen ............................. 260/409
4,551,564   11/1985  Otte et al. ....................... 568/834
4,585,632   4/1986   Schneider et al. ............... 423/239

FOREIGN PATENT DOCUMENTS 2023832    8/1970    France .
137 526    12/1986   Poland .
97/10202   3/1997    WIPO .

*Primary Examiner*—Michael L. Shippen
*Attorney, Agent, or Firm*—Keil & Weinkauf

[57] ABSTRACT

A process for hydrogenating aromatic compounds in which at least one hydroxyl group is bonded to an aromatic ring comprises bringing at least one of these compounds into contact with free hydrogen in the presence of a catalyst, wherein the catalyst comprises ruthenium and, if desired, at least one metal of transition groups I, VII and VIII in an amount of from 0.01 to 30% by weight, preferably from 0.2 to 15% by weight, based on the total weight of the catalyst, applied to a support, where the support has a mean pore diameter of at least 0.1 μm, preferably at least 0.5 μm, and a surface area of at most 15 m$^2$/g, preferably at most 10 m$^2$/g.

18 Claims, No Drawings

HYDROGENATION OF AROMATIC COMPOUNDS IN WHICH AT LEAST ONE HYDROXYL GROUP IS BONDED TO AN AROMATIC RING

The present invention relates to a process for hydrogenating aromatic compounds in which at least one hydroxyl group is bonded to an aromatic ring.

The present invention relates in particular to a process for hydrogenating aromatic compounds in which, in addition to at least one hydroxyl group, at least one unsubstituted or substituted $C_1$–$C_{10}$-alkyl and/or alkoxy radical is bonded to an aromatic ring. Preference is given to using monoalkyl-substituted phenols in the process of the present invention. The monocyclic or polycyclic aromatic compounds are here hydrogenated to give the corresponding cycloaliphatic compounds, with the hydroxyl groups being retained, with the aid of catalysts comprising ruthenium and, if desired, at least one further metal of transition groups I, VII and VIII on a support.

Cycloaliphatic alcohols, in particular alkylcyclohexanols, are important intermediates for the preparation of various fragrances, drugs and other organic fine chemicals.

It is known that alkylcyclohexanols can be prepared by catalytic hydrogenation of the corresponding alkylphenols. The hydrogenation of alkylphenols to give the corresponding alkylcyclohexanols in the presence of hydrogenation catalysts, in particular catalysts applied to supports, has been described many times.

Catalysts which have been used are, for example, metallic rhodium, ruthenium, palladium or nickel on catalyst supports. Catalyst supports which have been used are carbon, barium carbonate and, in particular, aluminum oxide.

PL 137 526 describes the hydrogenation of p-tert-butylphenol to give p-tert-butylcyclohexanol using a nickel catalyst.

DE-A1-34 01 343 describes a process for preparing 2- and 4-tert-butylcyclohexanol from 2- and 4-tert-butylphenol by catalytic hydrogenation. The hydrogenation is carried out in two stages using a palladium catalyst on an $Al_2O_3$ support in a first stage and a ruthenium catalyst on an $Al_2O_3$ support in the second stage. The metal content on the support was here from 0.1 to 5% by weight. The supports are not further specified. The reaction was carried out at a pressure of 300 bar with product recirculation. The cis-tert-butylphenols were preferentially obtained, with from 0.1 to 0.5% of by-products being formed.

U.S. Pat. No. 2,927,127 describes a process for preparing p-tert-butylcyclohexanol and esters thereof by catalytic hydrogenation of p-tert-butylphenol. Catalysts used were 5% of rhodium on carbon, 5% of palladium on barium carbonate or 5% of ruthenium on carbon. When using ruthenium on carbon, the reaction was carried out at a pressure of from 70 to 120 bar and at from 74 to 93° C. 66% of cis isomer were obtained as hydrogenation product.

DE-A1-29 09 663 describes a process for preparing cis-alkylcyclohexanols by catalytic hydrogenation of the corresponding alkylphenols. The catalyst used was ruthenium on an $Al_2O_3$ support, with the catalyst being supposed to have a specific surface area in the range from 100 to 300 $m^2/g$ and a particle size distribution with a maximum particle size of <0.15 mm. The reaction was carried out at a pressure of 40, 60 or 80 bar. The product obtained comprised predominantly cis-alkylcyclohexanols with from 0.1 to 1% of alkylbenzene as by-product.

It is an object of the present invention to provide a process for hydrogenating compounds in which at least one hydroxyl group and preferably at least one unsubstituted or substituted $C_1$–$C_{10}$-alkyl radical and/or alkoxy radical is bonded to an aromatic ring to give the corresponding cycloaliphatic compounds in very high yield or with virtually complete conversion. A further object of the invention is to provide a process for hydrogenating aromatic compounds in which at least one hydroxyl group and preferably at least one unsubstituted or substituted $C_1$–$C_{10}$-alkyl radical and/or alkoxy radical is bonded to an aromatic ring to give the corresponding cycloaliphatic compounds with only a minimal proportion of by-products or decomposition products being obtained in the hydrogenation. A further object of the present invention is to provide a process for hydrogenating aromatic compounds in which at least one hydroxyl group and preferably at least one unsubstituted or substituted $C_1$–$C_{10}$-alkyl radical and/or alkoxy radical is bonded to an aromatic ring with high throughputs over the catalyst and long catalyst operating lives being made possible. A further object of the present invention is to provide a single-stage process for hydrogenating aromatic compounds in which at least one hydroxyl group and prefer-ably at least one unsubstituted or substituted $C_1$–$C_{10}$-alkyl radical and/or alkoxy radical is bonded to an aromatic ring. A further object of the present invention is to provide a process for hydrogenating aromatic compounds in which at least one hydroxyl group and preferably at least one unsubstituted or substituted $C_1$–$C_{10}$-alkyl radical and/or alkoxy radical is bonded to an aromatic ring with the cycloaliphatic compounds obtained being able to be further processed without further purification steps. A further object of the present invention is to provide a process for hydrogenating aromatic compounds in which at least one hydroxyl group and preferably at least one unsubstituted or substituted $C_1$–$C_{10}$-alkyl and/or alkoxy radical are bonded to an aromatic ring to give the corresponding cycloaliphatic compounds with predominantly trans-cycloaliphatic compounds being formed.

We have found that these objects are achieved by a process for hydrogenating aromatic compounds in which at least one hydroxyl group is bonded to an aromatic ring, which comprises bringing at least one of these compounds into contact with free hydrogen in the presence of a catalyst, wherein the catalyst comprises ruthenium and, if desired, at least one metal of transition groups I, VII and VIII in an amount of from 0.01 to 30% by weight, preferably from 0.2 to 15% by weight, based on the total weight of the catalyst, applied to a support, where the support has a mean pore diameter of at least 0.1 $\mu$m, preferably at least 0.5 $\mu$m, and a surface area of at most 15 $m^2/g$, preferably at most 10 $m^2/g$. Particular embodiments are described below.

According to the present invention, it has been found that in place of the known hydrogenation catalysts which are typically applied to mesoporous supports having a high surface area in order to achieve a high catalyst activity it is possible to use catalysts on macroporous supports. Despite the low surface area of the catalysts which comprise ruthenium and, if desired, one or more further metals of transition groups I, VII and VIII, aromatic compounds in which at least one hydroxyl group and preferably at least one unsubstituted or substituted $C_1$–$C_{10}$-alkyl radical and/or alkoxy radical is bonded to an aromatic ring can be hydrogenated with high selectivity to give the corresponding cycloaliphatic alcohols, with predominantly trans-cycloaliphatic compounds being formed. The formation of by-products is minimal in the process of the present invention. In particular, the formation of aromatic compounds, in particular alkylaromatics or alkylbenzenes from alkylphenols, is virtu-ally completely avoided.

In addition, high throughputs over the catalyst and long catalyst operating lives can be achieved. The throughput over the catalyst is here the space-time yield of the process, ie. the amount of starting material reacted per unit time and per amount of catalyst present. Operating life is the time or the amount of reacted starting material which can be passed over a catalyst without its properties being impaired and without the product properties being significantly changed.

COMPOUNDS

The process of the present invention enables aromatic compounds in which at least one hydroxyl group and preferably at least one unsubstituted or substituted $C_1$–$C_{10}$-alkyl radical and/or alkoxy radical is bonded to an aromatic ring to be hydrogenated to give the corresponding cycloaliphatic compounds. The aromatic compounds can here be monocyclic or polycyclic aromatic compounds. The aromatic compounds contain at least one hydroxyl group which is bonded to an aromatic ring; the simplest compound of this group is phenol. The aromatic compounds preferably have one hydroxyl group per aromatic ring. The aromatic compounds can be substituted on the aromatic ring or rings by one or more alkyl and/or alkoxy radicals, preferably $C_1$–$C_{20}$-alkyl and/or alkoxy radicals, particularly preferably $C_1$–$C_{10}$-alkyl radicals, in particular methyl, ethyl, propyl, isopropyl, butyl, isobutyl or tert-butyl radicals; among the alkoxy radicals, preference is given to the $C_1$–$C_8$-alkoxy radicals. The aromatic ring or rings as well as the alkyl and alkoxy radicals may be substituted by halogen atoms, in particular fluorine atoms, or have other suitable inert substituents.

The compounds which can be hydrogenated according to the present invention preferably have at least one, preferably from one to four, in particular one, $C_1$–$C_{20}$-alkyl radical which is preferably located on the same aromatic ring as the hydroxyl group or groups. Preferred compounds are (mono) alkylphenols, where the alkyl radical can be in the o, m or p position relative to the hydroxyl group. Particular preference is given to trans-alkylphenols, also referred to as 4-alkylphenols, where the alkyl radical preferably has from 1 to 10 carbon atoms and is in particular a tert-butyl radical. The preferred compound is 4-tert-butylphenol. Polycyclic aromatic compounds which can be used according to the present invention are, for example, β-naphthol and α-naphthol.

The aromatic compound in which at least one hydroxyl group and preferably at least one unsubstituted or substituted $C_1$–$C_{10}$-alkyl radical and/or alkoxy radical is bonded to an aromatic ring can also have a plurality of aromatic rings which are linked via an alkylene radical, preferably a methylene group. The linking alkylene chain, preferably methylene group, can have one or more alkyl substituents which can be $C_1$–$C_{20}$-alkyl radicals, preferably $C_1$–$C_{10}$-alkyl radicals, particularly preferably methyl, ethyl, propyl, isopropyl, butyl, sec-butyl or tert-butyl radicals.

In these compounds, each of the aromatic rings can contain at least one bonded hydroxyl group. Examples of such compounds are bisphenols which are linked in the 4 position via an alkylene radical, preferably a methylene radical. A preferred example is bisphenol A in which two phenol molecules are linked in the 4 position via a dimethylmethylene group.

CATALYSTS

The catalysts used according to the present invention can be prepared industrially by applying ruthenium and, if desired, at least one metal of transition groups I, VII and VIII to a suitable support. The application can be achieved by immersing the support in aqueous metal salt solutions such as ruthenium salt solutions, by spraying appropriate metal salt solutions onto the support or by other suitable methods. Salts suitable for preparing the ruthenium salt solutions and as metal salts of transition groups I, VII and VIII are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts comprising not only ruthenium but also further metals on the support, the metal salts or metal salt solutions can be applied simultaneously or in succession.

The supports coated or impregnated with the ruthenium salt or metal salt solution are then dried, preferably at from 100° C. to 150° C., and if desired calcined at from 200° C. to 600° C.

Subsequently, the coated supports are activated by treating the coated supports in a gas stream comprising free hydrogen at from 30 to 600° C., preferably from 150 to 450° C. The gas stream preferably comprises from 50 to 100% by volume of $H_2$ and from 0 to 50% by volume of $N_2$.

If not only ruthenium but also one or more other metals of transition groups I, VII and VIII are applied to the supports and the application is carried out in succession, the support can be dried at from 100 to 150° C. and if desired calcined at from 200 to 600° C. after each application or impregnation. The order in which the metal salt solutions are applied or the support is impregnated with the solutions can be selected as desired.

If not only ruthenium but also one or more further metals of transition groups I, VII and VIII are applied to the support, preference is given to using copper, rhenium, cobalt, nickel or mixtures thereof.

The ruthenium salt solution or metal salt solution is applied to the support or supports in such an amount that from 0.01 to 30% by weight, based on the total weight of the catalyst, of ruthenium and any other metal or metals of transition groups I, VII and VIII are present, in applied form, on the support. This amount is preferably from 0.2 to 15% by weight, particularly preferably about 0.5% by weight.

The total metal surface area on the catalyst is preferably from 0.01 to 10 $m^2$/g, particularly preferably from 0.05 to 5 $m^2$/g, in particular from 0.05 to 3 $m^2$ per g of the catalyst.

SUPPORTS

The support materials which can be used for preparing the catalysts used according to the present invention are preferably ones which are macroporous and have a mean pore diameter of at least 0.1 μm, preferably at least 0.5 μm, and a surface area of at most 15 $m^2$/g, preferably at most 10 $m^2$/g, particularly preferably at most 5 $m^2$/g, in particular at most 3 $m^2$/g. The mean pore diameter of the support is preferably in a range from 0.1 to 200 μm, in particular from 0.5 to 50 μm. The surface area of the support is preferably from 0.2 to 15 $m^2$/g, particularly preferably from 0.5 to 10 $m^2$/g, in particular from 0.5 to 5 $m^2$/g, especially from 0.5 to 3 $m^2$ per g of the support.

The surface area of the support is determined by the BET method by $N_2$ adsorption, in particular in accordance with DIN 66131. The mean pore diameter and the pore size distribution are determined by Hg porosimetry, in particular in accordance with DIN 66133. Preferably, the pore size distribution of the support can be approximately bimodal, with the pore diameter distribution with maxima at about 0.6 µm and about 20 µm in the bimodal distribution being a specific embodiment of the invention.

Particular preference is given to a support having a surface area of about 1.75 m²/g which has this bimodal distribution of the pore diameter. The pore volume of this preferred support is preferably about 0.53 ml/g.

Examples of macroporous support material which can be used are activated carbon, silicon carbide, aluminum oxide, silicon dioxide, titanium dioxide, zirconium dioxide, magnesium oxide, zinc oxide or mixtures thereof. Preference is given to aluminum oxide and zirconium dioxide.

The catalysts used according to the present invention preferably display a high reactivity, selectivity and operating life. When using the catalysts of the present invention in the hydrogenation, the hydrogenation products are preferably obtained in high yield and purity, making a subsequent purification superfluous. The conversion is virtually quantitative, the residual aromatics content is preferably less than 0.01% by weight, based on the total amount of product. The hydrogenation product obtained can thus be passed directly to further processing without having to be purified.

SOLVENTS OR DILUENTS

In the process of the present invention, the hydrogenation can be carried out in the absence of a solvent or diluent, ie. according to one embodiment it is not necessary to carry out the hydrogenation in solution. However, preference is given to using a solvent or diluent in the process of the present invention. The solvent or diluent used can be any suitable solvent or diluent. The selection is not critical: for example, according to one embodiment, the solvent or diluent can also contain small amounts of water. Examples of suitable solvents or diluents include straight-chain or cyclic ethers such as tetrahydrofuran or dioxane, and also aliphatic alcohols in which the alkyl radical preferably has from 1 to 10 carbon atoms, in particular from 3 to 6 carbon atoms. Examples of preferred alcohols are i-propanol, n-butanol, i-butanol and n-hexanol. Mixtures of these or other solvents or diluents can likewise be used. The solvent or diluent can be used in appropriate amounts, with preference being given to amounts which lead to a 10–70% strength by weight solution of the compounds to be hydrogenated.

The solvent used can also be, particularly preferably, the product formed in the hydrogenation by the process of the present invention, if desired in combination with other solvents or diluents. In this case, part of the product formed in the hydrogenation process can be mixed into the compounds to be hydrogenated. The amount of the hydrogenation product mixed in as solvent or diluent is preferably from 1 to 30 times, particularly preferably from 5 to 20 times, in particular from 5 to 10 times, the weight of the compounds to be hydrogenated.

HYDROGENATION

The hydrogenation is carried out at appropriate pressures and temperatures. Preference is given to pressures above 50 bar, preferably from 150 to 300 bar. Preferred temperatures are in a range from 100 to 270° C., preferably from 150 to 220° C.

The hydrogenation process can be carried out continuously or as a batch process. In the continuous process, part of the hydrogenation product leaving the reactor can be recirculated to the reactor feed upstream of the reactor. Here, the amount of hydrogenation product leaving the reactor which is recirculated as solvent is such that the abovementioned mixing ratios are achieved. The remaining amount of hydrogenation product is taken off. In a continuous process procedure, the amount of the compound or compounds to be hydrogenated is preferably in the range from 0.05 to 3 l per liter of catalyst per hour, preferably from 0.1 to 1 l per liter of catalyst per hour.

The hydrogenation gases used can be any gases which comprise free hydrogen and do not have any harmful amounts of catalyst poisons, for example CO. For example, reformer waste gases can be used. Preference is given to using pure hydrogen as hydrogen gas.

When using the hydrogenation catalyst of the present invention, in particular in the hydrogenation of 4-alkyl- or 4-alkoxy-substituted phenols as described above, predominantly trans-cycloaliphatic compounds are obtained. The proportion of trans-cycloaliphatic compounds is, according to one embodiment of the invention, at least 60%, preferably at least 65%.

The examples below illustrate the invention.

EXAMPLE 1

Preparation of the Catalyst

A macroporous aluminum oxide support in the form of 8×8×3 mm rings having a surface area determined by the BET method of 1.75 m²/g, a pore volume of 0.531 ml/g and a pore diameter of 0.6 µm and 20 µm in a bimodal distribution was impregnated with an aqueous ruthenium(III) nitrate solution having a concentration of from 0.7 to 1% of metal, based on the weight of the solution. The volume of solution absorbed by the support corresponded approximately to the pore volume of the support used. The support impregnated with the ruthenium (III) nitrate solution was then dried at 120° C. while being kept in motion and reduced at 200° C. in a stream of hydrogen. The catalyst thus prepared contained 0.5% by weight of ruthenium, based on the total weight of the catalyst, and had a ruthenium surface area of 0.76 m²/g, determined by $H_2$-pulse chemisorption (Puls Chemiesorp 2700, 35° C.).

EXAMPLE 2

3.2 l of the catalyst prepared as described in Example 1, which contained 0.5% by weight of ruthenium on a macroporous $Al_2O_3$ support, were placed in an electrically heated flow-through reactor which was equipped with a separator. Subsequently, without prior activation of the catalyst, a hydrogenation of p-tert-butylphenol was carried out at 260 bar and 180° C. The p-tert-butylphenol was fed to the reactor as a 50% strength by weight solution in THF. 2500 g/h of this solution were passed through the flow-through reactor. The hydrogenation was carried out continuously in the upflow mode. The amount of p-tert-butylphenol solution in THF fed continuously to the reactor corresponded to a throughput over the catalyst of about 400 g/l of catalyst×h (800 g of the 50% strength by weight solution). After distilling off the solvent, the hydrogenation product had, on average, the following composition (in % by weight of the total hydrogenation product):

<0.01% of 4-tert-butylcyclohexane
67.0% of trans-4-tert-butylcyclohexanol
32.9% of cis-4-tert-butylcyclohexanol
<0.01% of p-tert-butylphenol
<0.1% of unknown compounds

EXAMPLE 3

A hydrogenation was carried out as described in Example 2, but 3500 g/h of the 50% strength by weight solution of p-tert-butylphenol in THF were passed through the reactor. The temperature was 200° C. instead of 180° C. After distilling off the solvent, the hydrogenation product had, on average, the following composition:

<0.01% of 4-tert-butylcyclohexane
68.8% of trans-4-tert-butylcyclohexanol
31.0% of cis-4-tert-butylcyclohexanol
<0.01% of p-tert-butylphenol
<0.2% of unknown compounds

EXAMPLE 4

A hydrogenation was carried out as described in Example 2, but a 50% strength by weight solution of p-tert-butylphenol in i-butanol was used in place of a 50% strength by weight solution in THF.

After distilling off the solvent, the hydrogenation product had, on average, the following composition:

<0.01% of 4-tert-butylcyclohexane
67.5% of trans-4-tert-butylcyclohexanol
32.4% of cis-4-tert-butylcyclohexanol
<0.01% of p-tert-butylphenol
<0.1% of unknown compounds

EXAMPLE 5

500 ml of the macroporous catalyst from Example 1 (0.5% by weight of Ru on $Al_2O_3$) were placed in a catalyst basket in a pressure autoclave having a capacity of 3.5 l. 2 kg of a 50% strength by weight solution of bisphenol A in THF were introduced into the autoclave.

The autoclave was subsequently pressurized with 200 bar of hydrogen and the hydrogenation was carried out at 150° C. for 5 hours.

After the reaction, the mixture was cooled to room temperature, depressurized to ambient pressure and the solvent was distilled off. The conversion to the corresponding cycloaliphatic diol isomer mixture was quantitative, with the residual aromatics content being less than 0.01% by weight.

The experimental results of the continuous or discontinuous hydrogenation using the catalyst of the present invention show that aromatic compounds in which at least one hydroxyl group and an unsubstituted or substituted $C_1$–$C_{10}$-alkyl radical are bonded to an aromatic ring give the cycloaliphatic hydrogenation products and only a minimal proportion of by-products. In the hydrogenation of p-tert-butylphenol, predominantly trans-4-tert-butylcyclohexanol is formed; the amount of trans compound formed is at least twice as much as the amount of cis compound formed.

We claim:

1. A process for hydrogenating aromatic compounds in which at least one hydroxyl group is bonded to an aromatic ring, which comprises bringing said aromatic compounds into contact with free hydrogen in the presence of a catalyst, wherein the catalyst comprises
   a) ruthenium, and
   b) a macroporous support, which has
      $b_1$) a mean pore diameter of a least 0.1 µm, and
      $b_2$) a surface area of at most 15 $m^2$/g.

2. The process of claim 1, wherein the aromatic compound, in addition to at least one hydroxyl group, carries at least one unsubstituted or substituted $C_1$–$C_{10}$-alkyl and/or alkoxy radical.

3. The process of claim 1, wherein the aromatic compound is a phenol which is substituted by a $C_1$–$C_{10}$-alkyl radical, where the alkyl radical may be substituted by an aromatic radical.

4. The process of claim 1, wherein the hydrogenation is carried out in the presence of a solvent or a diluent.

5. The process of claim 4, wherein the solvent or diluent is the hydrogenation product which is present in an amount of from 1 to 30 times the weight of the compound to be hydrogenated.

6. The process of claim 1, wherein the catalyst further has one or both of the following features:

the pore size distribution of the macroporous support is approximately bimodal, the macroporous support is selected from the group consisting of activated carbon, silicon carbide, aluminium oxide, silicon oxide, titanium dioxide, zirconium dioxide, magnesium oxide, zinc oxide and mixtures thereof.

7. The process of claim 1, wherein the catalyst comprises a macroporous support having a mean pore diameter of at least 0.5 µm.

8. The process of claim 1, wherein the catalyst comprises a macroporous support having a surface area of at most 10 $m^2$/g.

9. The process of claim 1, wherein the catalyst comprises a macroporous support which is selected from the group consisting of aluminium oxide and zirconium dioxide.

10. The process of claim 1, wherein the catalyst comprises
    a) 0.5% by weight, based on the total weight of the catalyst, of ruthenium, having a surface area on the macroporous support of about 0.76 $m^2$/g of the catalyst, and
    b) a macroporous aluminium oxide support having a surface area of about 1.75 $m^2$/g, a pore volume of about 0.531 ml/g and an approximately bimodal pore size distribution with pore diameters of about 0.6 µm and about 20 µm.

11. The process of claim 1, wherein the catalyst further comprises
    c) from 0.001 to 30% by weight, based on the total weight of the catalyst, of at least one metal of transition groups I, VII and VIII.

12. The process of claim 11, wherein the catalyst comprises from 0.2 to 15% by weight, based on the total weight of the catalyst, of at least one metal of transition groups I, VII and VIII.

13. The process of claim 11, wherein the catalyst further has one or more of the following features:

the pore size distribution of the macroporous support is approximately bimodal, the macroporous support is selected from the group consisting of activated carbon, silicon carbide, aluminium oxide, silicon oxide, titanium dioxide, zirconium dioxide, magnesium oxide, zinc oxide and mixtures thereof, the metal or metals of transition groups I, VII and VIII is/are selected from the group consisting of copper, rhenium, cobalt, nickel and mixtures thereof, the metal applied to the macroporous support has a surface area of from 0.01 $m^2$/g of the catalyst.

14. The process of claim 11, wherein the catalyst comprises a macroporous support having a mean pore diameter of at least 0.5 µm.

15. The process of claim 11, wherein the catalyst comprises a macroporous support having a surface area of at most 10 $m^2$/g.

16. The process of claim 11, wherein the catalyst comprises a macroporous support which is selected from the group consisting of aluminium oxide and zirconium dioxide.

17. The process of claim 11, wherein the metal applied to the macroporous support has a surface area of from 0.05 to 5 m$^2$/g of the catalyst.

18. The process of claim 11, wherein the catalyst comprises a) 0.5% by weight, based on the total weight of the catalyst, of ruthenium, having a surface area on the macroporous support of about 0.76 m$^2$/g of the catalyst, and b) a macroporous aluminium oxide support having a surface area of about 1.75 m$^2$/g, a pore volume of about 0.531 ml/g and an approximately bimodal pore size distribution with pore diameters of about 0.6 $\mu$m and about 20 $\mu$m.

* * * * *